United States Patent [19]
Enhsen et al.

[11] Patent Number: 5,486,626
[45] Date of Patent: Jan. 23, 1996

[54] PROCESS FOR THE PREPARATION OF 3β-AMINOCHOLANIC ACID DERIVATIVES

[75] Inventors: Alfons Enhsen, Büttelborn; Heiner Glombik, Hofheim/Ts.; Werner Kramer, Mainz; Günther Wess, Erlensee, all of Germany

[73] Assignee: Hoechst Aktiengesellschaft, Frankfurt am Main, Germany

[21] Appl. No.: 206,321

[22] Filed: Mar. 7, 1994

[30] Foreign Application Priority Data

Mar. 9, 1993 [DE] Germany .................... 43 07 305.0

[51] Int. Cl.[6] ........................................ C07J 41/00
[52] U.S. Cl. ................................................ 552/521
[58] Field of Search ...................................... 552/521

[56] References Cited

PUBLICATIONS

March, *Advanced Organic Chemistry*, p. 388, 1977.
"Amines cycliques des acides biliaires. Premiere partie: Monoamines(*)" J. Redel, et al., Bull. Soc. Chim. Fr., pp. 877–883 (1949).
"Basic Bile Acids. V. On the Syntheses and Properties of Basic Bile Acids and their Derivatives", Yasuo Satoh, Bull. Chem. Soc. Jap. 38(10):1581–1585 (1965).

*Primary Examiner*—Gary L. Geist
*Assistant Examiner*—Catherine S. Kilby Scalzo
*Attorney, Agent, or Firm*—Finnegan, Henderson, Farabow, Garrett & Dunner

[57] ABSTRACT

Process for the preparation of 3β-aminocholanic acid derivatives

A process for the preparation of 3β-aminocholanic acid derivatives of the formula II

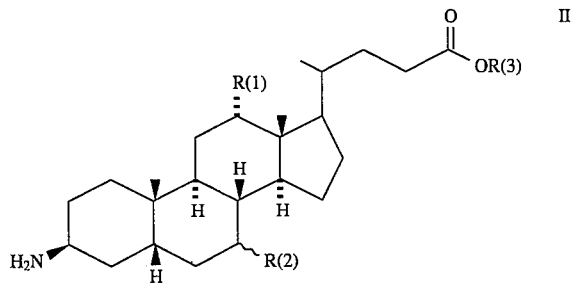

wherein R(1), R(2) and R(3) have the meanings given, starting from the corresponding 3β-hydroxycholanic acid esters, is described.

4 Claims, No Drawings

PROCESS FOR THE PREPARATION OF 3β-AMINOCHOLANIC ACID DERIVATIVES

DESCRIPTION

Process for the preparation of 3β-aminocholanic acid derivatives

3β-Aminocholanic acid esters are gaining increasing importance as useful intermediate products for the preparation of compounds for a number of pharmaceutical uses. They are employed, for example, as synthesis units for the preparation of active compound-bile acid conjugates (EP-A-0 417 725=U.S. patent application Ser. No. 07/806,799). The bile acid radical functions as a carrier in these conjugates and allows liver-selective transportation of the covalently bonded active compound via the enterohepatic circulation. 3β-Aminocholanic acid esters are also used as important synthones in the synthesis of bile acid resorption inhibitors (cf., for example, EP-A-0 489 423= U.S. patent application Ser. No. 07/802,413). These bile acid derivatives are selective inhibitors of the intestinal bile acid transportation system and therefore lead to an interruption in the enterohepatic circulation and thus to a reduction in the plasma cholesterol level.

In the literature, several processes are described for the synthesis of 3-aminocholanic acid derivatives of the formula I

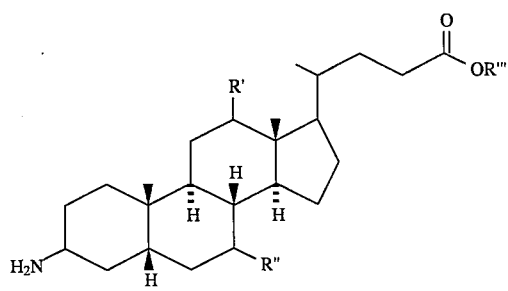

in which R', R" and R''' have, for example, the meanings given in the literature references mentioned below.

Thus, the corresponding oxime is prepared from 3-keto-cholanic acids. The oxime function can be reduced with sodium/amyl alcohol (Redel et al., Bull. Soc. Chim. Fr. 877, (1949)) or under catalytic conditions with hydrogen (Satoh, Bull. Chem. Soc. Jap., 1965, 38, 1581). The disadvantage of these processes is that isomeric mixtures of the 3α- and 3β-aminocholanic acid derivatives of the formula I are obtained in all cases and have to be separated and purified in an expensive manner. The stereoselectivity varies with the substrates and the reaction conditions, and these processes furthermore give only moderate yields.

According to a process which is also described, after activation of the 3-hydroxyl function of 3-hydroxycholanic acid esters, for example by reaction with methanesulfonyl chloride, the 3-azidocholanic acid derivative is obtained by nucleophilic substitution with sodium azide.

The stereochemistry of the reaction is unambiguous. Subsequent reduction of the azido group leads to 3-aminocholanic acid esters. However, the reaction procedure during the azide exchange is problematic, since the azide compounds are exposed to high temperatures (of about 130° C.) for a relatively long time in this process. Furthermore, the yields are only in the range from 30 to 50%.

It has now been found, surprisingly, that the compounds of the formula II can be prepared stereoselectively in high yields and by a reliable process from starting compounds which are readily available. Key components for the synthesis of useful medicaments are thus made available by an economic route.

The invention relates to a process for the preparation of 3β-aminocholanic acid derivatives of the formula II

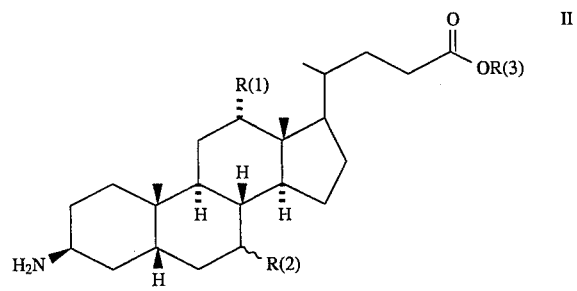

in which R(1) is H or OH,

R(2) is H, α-OH or β-OH and R(3) is an unbranched $C_1$–$C_4$-alkyl radical or a branched $C_3$–$C_4$-alkyl or a benzyl radical, and of salts thereof with mineral acids, which comprises a) reacting a 3α-hydroxycholanic acid ester of the formula III

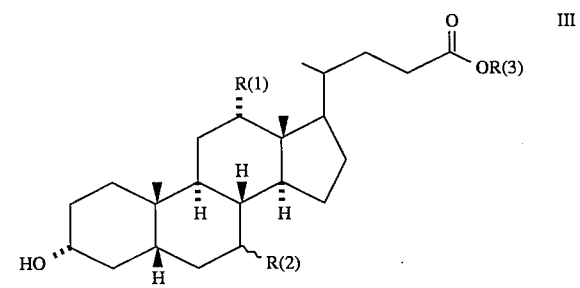

with phthalimide to give the 3β-phthalimido derivative of the formula IV

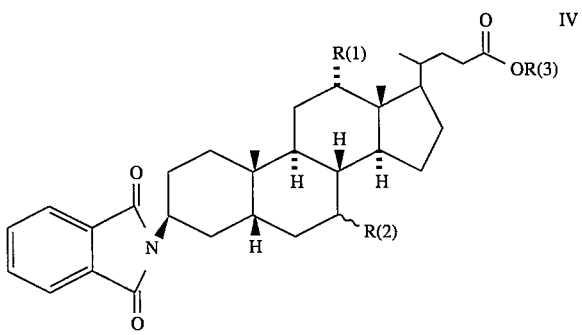

b) reacting a resulting 3β-phthalimidocholanic acid ester of the formula IV with hydrazine hydrate or phenylhydrazine and c) splitting the phthalimide group by treating the reaction product with an aqueous solution of a mineral acid, an acid addition salt of the compound II with the mineral acid being formed, and d) if appropriate converting a resulting salt into the free compound.

The reaction of the compound III with phthalimide is expediently carried out under the conditions of the Mitsunobu reaction (Mitsunobu, Synthesis 1, 1981; Org. React.

Vol. 42,335 (1992)) in the presence of a suitable phosphine, preferably triphenylphosphine, and azodicarboxylic acid diethyl (or diisopropyl) ester. The reaction is expediently carried out in a suitable solvent, such as tetrahydrofuran or also dioxane, at temperatures of 20° to 50° C.

The free compound of the formula II is obtained from the salts by customary methods.

The advantage of this reaction is that no protective groups are necessary for hydroxyl groups in positions 7 or 12, the reaction is regioselective and takes place only in the 3-position, and furthermore it is diastereoselective and the 3β-phthalimide derivative exclusively is formed in high yields from the 3α-hydroxyl group of the steroid.

Mineral acids are, for example, sulfuric acid, nitric acid and hydrochloric acid. An aqueous solution of hydrochloric acid is preferably used in the process according to the invention.

Esters of the formula III are prepared from the corresponding acids by customary processes.

perature does not exceed 10° to 15° C. After the addition, the mixture is subsequently stirred at about 10° C. for a further 15 minutes. 600 g (1.47 mol) of cholic acid are then introduced at about 5° C. The ice-bath is removed, and after a further hour, while stirring, the reaction is ended. The reaction mixture is slowly added to 12 l of water. The mixture is stirred for a further 2 hours and then filtered with suction, and the residue is rinsed with 3 l of water. The crystalline substance is dried in vacuo at 50° C. 610 g (98%) of methyl cholate (melting point 154° C.) are obtained.

The invention is illustrated in more detail by the following examples:

EXAMPLE 1

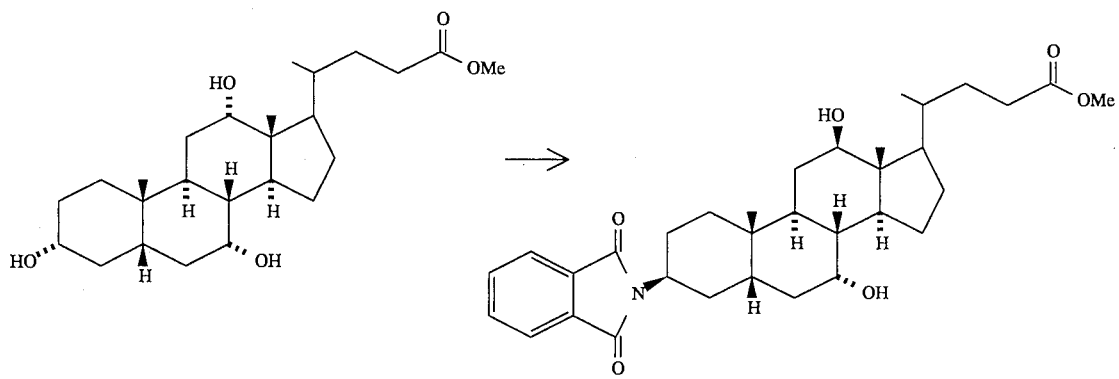

Preparation of the starting compounds of the formula III using the example of methyl cholanate (Fieset et al., J. Am. Chem. Soc. 74, 1952, 3309)

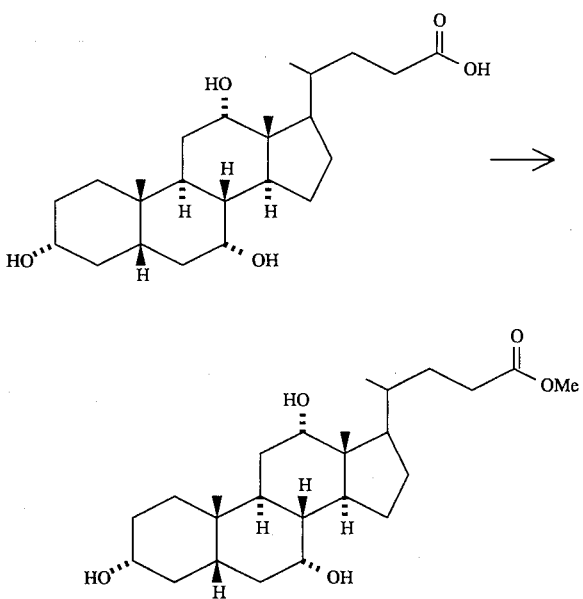

450 ml of acetyl chloride are slowly added dropwise to 4.5 l of methanol, while cooling with ice, such that the tem- A mixture of 500 g (1.18 mol) of methyl cholate, 341 g (1.30 mol) of triphenylphosphine and 191 g (1.29 mol) of phthalimide is heated to 40° C. in 3.0 l of absolute THF. A solution of 400 ml (2.57 mol) of azodicarboxylic acid diethyl ester and 200 ml of THF is slowly added dropwise, while stirring and under an inert gas, such that the temperature does not exceed 40° to 50° C. (gentle cooling necessary). After the addition, the mixture is stirred at about 45° C. for a further 1.5 hours. The reaction mixture is concentrated*. The residue is heated to the boiling point in 15 l of isopropanol and the mixture is stirred until all the constituents are finely dispersed. The mixture is left to stand for 48 hours and filtered with suction and the residue is washed with 10 l of isopropanol. After drying in vacuo at 60° C., 527 g (81%) of product are obtained. The compound can be reacted without further purification to give the next stage*. (After concentration, the crude product can also be chromatographed over silica gel).

$R_f$=0.61, mobile phase: chloroform/MeOH 95:5

MS (FAB, 3-NBA/LiCl) $C_{33}H_{45}NO_6$ (551): 558 (M+Li$^+$)

EXAMPLE 2

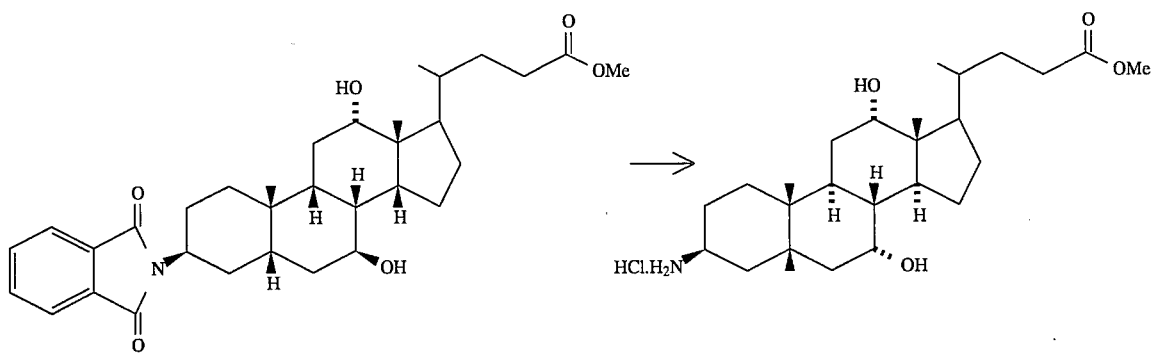

200 g (0.36 tool) of Example 1 are dissolved in 1.6 l of methanol, 60 ml of 80% strength hydrazine hydrate are added and the mixture is heated under reflux for 3 hours. The reaction mixture is cooled to 40° C. and 480 ml of 2N hydrochloric acid are added rapidly until a pH of about 2 to 3 is reached. After a further 30 minutes at 40° C., the mixture is cooled to −5° C. and by-products are filtered off with suction. The resulting solution is brought to pH 6 to 7 with sodium bicarbonate (about 35 g). It is then concentrated until the total volume is still about 500 ml. The residue is filtered off with suction, washed twice with in each case 500 ml of water and then twice with in each case 500 ml of ethyl acetate and dried in a drying cabinet at 60° C. The yield is 117 g (70%).

$R_f$=0.28, mobile phase: $CHCl_3$/MeOH 7:3, 5% $NEt_3$
MS (FAB, 3-NBA/LiCl) $C_{25}H_{43}NO_4$ (421): 428 (M+Li$^+$)

Examples 3 to 7 are obtained analogously to Example 1 and Examples 8 to 12 are obtained analogously to Example 2:

| Example | Structure | Starting compound | MS FAB, 3-NBA/LiCl | $R^f$ (mobile phase) |
|---|---|---|---|---|
| 3 | 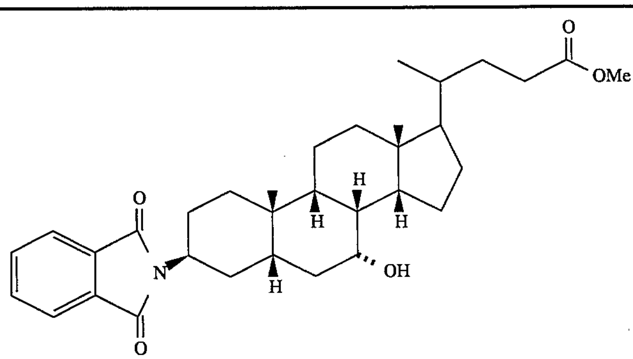 | Methyl chenodeoxycholate | $C_{33}H_{45}NO_5$ (535) 542 (M + Li$^+$) | 0.72 (cyclohexane/ ethyl acetate 1:1) |
| 4 | 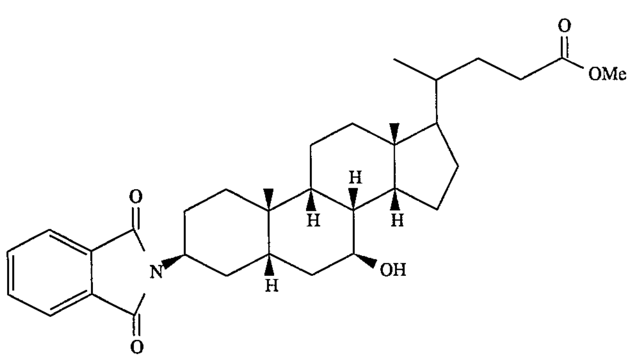 | Methyl ursodeoxycholate | $C_{33}H_{45}NO_5$ (535) 542 (M + Li$^+$) | 0.64 (cyclohexane/ ethyl acetate 1:1) |

-continued

| Example | Structure | Starting compound | MS FAB, 3-NBA/LiCl | $R^f$ (mobile phase) |
|---|---|---|---|---|
| 5 | (structure) | Methyl lithocholate | $C_{33}H_{45}NO_4$ (519) 526 (M + Li$^+$) | 0.55 (cyclohexane/ ethyl acetate 7:3) |
| 6 | (structure) | t-Butyl cholate | $C_{38}H_{51}NO_6$ (593) 600 (M + Li$^+$) | 0.54 (chloroform/ MeOH 95:5) |
| 7 | (structure) | Methyl ursocholate | $C_{33}H_{45}NO_6$ (551) 558 (M + Li$^+$) | 0.46 (cyclohexane/ ethyl acetate 7:3) |
| 8 | (structure) | Example 3 | $C_{25}H_{43}NO_3$ (405) 412 (M + Li$^+$) | 0.41 (CHCl$_3$/ MeOH 7:3, 5% NEt$_3$) |
| 9 | (structure) | Example 4 | $C_{25}H_{43}NO_3$ (405) 412 (M + Li$^+$) | 0.47 (CHCl$_3$/ MeOH 7:3, 5% NEt$_3$) |

-continued

| Example | Structure | Starting compound | MS FAB, 3-NBA/LiCl | $R^f$ (mobile phase) |
|---|---|---|---|---|
| 10 | 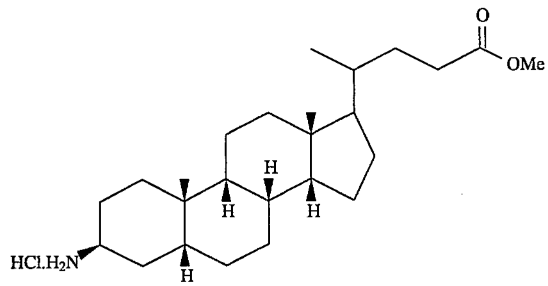 | Example 5 | $C_{25}H_{43}NO_2$ (389) 396 $(M+Li^+)$ | 0.53 ($CHCl_3$/MeOH 7:3, 5% $NEt_3$) |
| 11 | 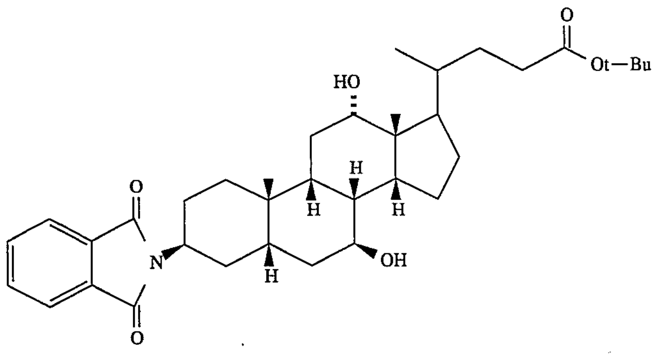 | Example 6 | $C_{28}H_{49}NO_4 \cdot HCl$ (500) 470 $(M-HCl+Li^+)$ | 0.70 (n-butanol/AcOH/$H_2O$ 8:2:1) |
| 12 | 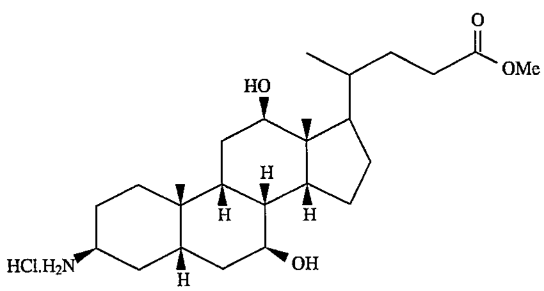 | Example 7 | $C_{25}H_{48}NO_4 \cdot HCl$ (458) 428 $(M-HCl+Li^+)$ | 0.26 (chloroform/MeOH 8:2) |

We claim:

1. A process for the preparation of a 3β-aminocholanic acid derivative of the formula II

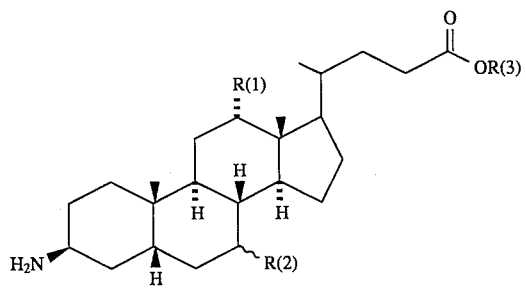

in which R(1) is H or OH,
R(2) is H, α-OH or β-OH and R(3) is an unbranched $C_1$–$C_4$-alkyl radical or a branched $C_3$–$C_4$-alkyl or a benzyl radical,
and of a salt thereof with a mineral acid, which comprises
a) reacting a 3α-hydroxycholanic acid ester of the formula III

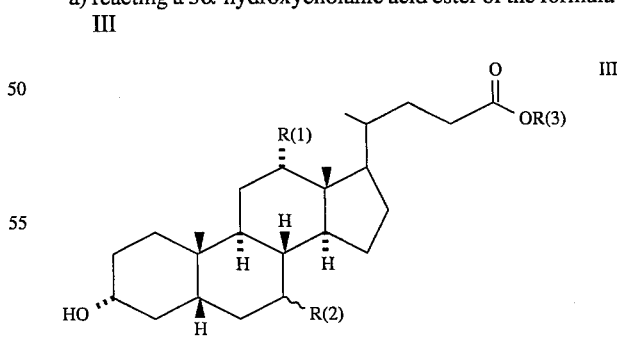

with phthalimide to give the 3β-phthalimido derivative of the formula IV

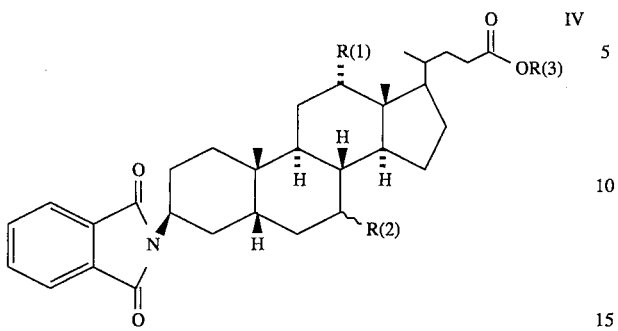

b) reacting a resulting 3β-phthalimidocholanic acid ester of the formula IV with hydrazine hydrate or phenylhydrazine and c) splitting the phthalimide group by treating the reaction product with an aqueous solution of a mineral acid, an acid addition salt of the compound II with the mineral acid being formed.

2. The process as claimed in claim 1, wherein the reaction of a compound of the formula III with phthalimide is carried out in the presence of a phosphine and azodicarboxylic acid diethyl or diisopropyl ester.

3. The process as claimed in claim 1, wherein aqueous hydrochloric acid is used as the mineral acid.

4. The process as claimed in claim 1, further comprising converting the acid addition salt of the compound II into a free compound of the formula II.

* * * * *

UNITED STATES PATENT AND TRADEMARK OFFICE
CERTIFICATE OF CORRECTION

PATENT NO. : 5,486,626
DATED : January 23, 1996
INVENTOR(S) : Alfons ENHSEN et al.

It is certified that error appears in the above-indentified patent and that said Letters Patent is hereby corrected as shown below:

In the Abstract, line 7, "3$\beta$-hydroxycholanic" should read --3$\alpha$-hydroxycholanic--.

Signed and Sealed this

Twenty-sixth Day of November 1996

Attest:

BRUCE LEHMAN

Attesting Officer

Commissioner of Patents and Trademarks